United States Patent
Lee et al.

(10) Patent No.: US 10,252,267 B2
(45) Date of Patent: *Apr. 9, 2019

(54) MICROFLUIDIC DEVICE FOR SIMULTANEOUSLY CONDUCTING MULTIPLE ANALYSES

(71) Applicant: SAMSUNG ELECTRONICS CO., LTD., Suwon-si (KR)

(72) Inventors: Beom-seok Lee, Hwaseong-si (KR); Yoon-kyoung Cho, Suwon-si (KR); Jong-myeon Park, Seoul (KR); Jeong-gun Lee, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/631,547

(22) Filed: Jun. 23, 2017

(65) Prior Publication Data
US 2017/0304826 A1    Oct. 26, 2017

Related U.S. Application Data

(63) Continuation of application No. 13/269,249, filed on Oct. 7, 2011, now Pat. No. 9,726,685, which is a
(Continued)

(30) Foreign Application Priority Data

Jun. 4, 2007  (KR) .................. 10-2007-0054628

(51) Int. Cl.
*B01L 3/00* (2006.01)
*F16K 99/00* (2006.01)
*G01N 35/00* (2006.01)

(52) U.S. Cl.
CPC ... *B01L 3/502738* (2013.01); *B01L 3/502746* (2013.01); *B01L 3/502753* (2013.01);
(Continued)

(58) Field of Classification Search
CPC ................. B01L 2300/0803; B01L 2400/0409
(Continued)

(56) References Cited

U.S. PATENT DOCUMENTS

| | | |
|---|---|---|
| 2001/0048895 A1 | 6/2001 | Virtanen |
| 2001/0055812 A1 | 12/2001 | Mian et al. |
| 2003/0156991 A1 | 8/2003 | Halas et al. |
| 2007/0092409 A1 | 4/2007 | Beatty et al. |

FOREIGN PATENT DOCUMENTS

| | | |
|---|---|---|
| EP | 1324042 A2 | 7/2003 |
| EP | 1901054 A2 | 3/2008 |

(Continued)

OTHER PUBLICATIONS

Communication dated Feb. 22, 2017 by the European Patent Office in counterpart European Patent Application No. 08157496.4.
(Continued)

*Primary Examiner* — Natalia Levkovich
(74) *Attorney, Agent, or Firm* — Sughrue Mion, PLLC

(57) ABSTRACT

Provided is a rotatable microfluidic device for conducting simultaneously two or more assays. The device includes a platform which can be rotated, a first unit which is disposed at one portion of the platform and detects a target material from a sample using surface on which a capture probe selectively binds to the target material is attached, and a second unit which is disposed at another portion of the platform and detects a target material included in the sample by a different reaction from the reaction conducted in the first unit.

20 Claims, 11 Drawing Sheets

Related U.S. Application Data continuation of application No. 12/128,981, filed on May 29, 2008, now abandoned.

(52) U.S. Cl.
CPC ........ *F16K 99/0001* (2013.01); *F16K 99/004* (2013.01); *F16K 99/0019* (2013.01); *F16K 99/0032* (2013.01); *F16K 99/0061* (2013.01); *G01N 35/00069* (2013.01); *B01L 3/502723* (2013.01); *B01L 2200/0684* (2013.01); *B01L 2200/10* (2013.01); *B01L 2300/0636* (2013.01); *B01L 2300/0803* (2013.01); *B01L 2300/0806* (2013.01); *B01L 2300/087* (2013.01); *B01L 2300/0867* (2013.01); *B01L 2400/0409* (2013.01); *B01L 2400/0677* (2013.01); *B01L 2400/084* (2013.01); *B01L 2400/086* (2013.01); *F16K 2099/0084* (2013.01)

(58) Field of Classification Search
USPC .................................................. 422/548, 72
See application file for complete search history.

(56) References Cited

FOREIGN PATENT DOCUMENTS

| | | |
|---|---|---|
| JP | 2001503854 A | 3/2001 |
| WO | 02/00347 A2 | 1/2002 |
| WO | 2004/079343 A2 | 9/2004 |
| WO | 2006/118420 A1 | 11/2006 |
| WO | 2007/005076 A1 | 1/2007 |
| WO | 2007/050418 A | 5/2007 |

OTHER PUBLICATIONS

European Patent Office, Communication dated Aug. 8, 2016 issued in counterpart European Patent Application No. 08157496.4.
European Patent Office, Communication dated May 6, 2015 issued in counterpart European Application No. 08157496.4.
Korean Intellectual Property Office, Communication dated Apr. 16, 2013 issued in counterpart Korean application No. 10-2007-0054628.
Park et al. "Multifunctional Microvalves Control by Optical Illumination on Nanoheaters and Its Application in Centrifugal Microfluidic Devices." Royal Society of Chemistry, vol. 7, Feb. 2007, pp. 557-564.

MICROFLUIDIC DEVICE FOR SIMULTANEOUSLY CONDUCTING MULTIPLE ANALYSES

CROSS-REFERENCE TO RELATED PATENT APPLICATIONS

This is Continuation of U.S. patent application Ser. No. 13/269,249, filed Oct. 7, 2011, which is a Continuation of U.S. patent application Ser. No. 12/128,981 filed May 29, 2008, which claims the benefit of Korean Patent Application No. 10-2007-0054628, filed on Jun. 4, 2007, in the Korean Intellectual Property Office, the disclosure of which is incorporated herein in its entirety by reference.

BACKGROUND OF THE INVENTION

1. Field of the Invention

The present invention relates to a rotatable microfluidic device, and more particularly, to a rotatable microfluidic device in which multiple analysis of a biological sample can be simultaneously conducted.

2. Description of the Related Art

A microfluidic structure that performs an independent function in a microfluidic device generally includes chambers that can contain a fluid, channels through which a fluid can flow, and valves that can control the flow of fluid, and can be configured by various combinations of the chambers, the channels, and the valves. An apparatus manufactured by disposing the microfluidic structure on a chip type substrate, so that experiments including several steps of treatments and manipulations of biochemical reactions can be performed on a small chip, is often referred to as a lab-on-a-chip.

In order to transport a fluid in a microfluidic structure, a driving pressure is necessary. The driving pressure can be capillary pressure or pressure supplied by an additional pump. Recently, a disk type microfluidic device in which a microfluidic structure is disposed on a disk-shaped platform to transport a fluid using centrifugal force and to perform a series of works has been proposed, which is referred to as a Lab CD or a Lab-on-a-disk. Efforts have been made to provide various disk types of microfluidic devices that can rapidly and accurately perform necessary work in a centrifugal force-based disk type platform.

Disk type microfluidic devices can be applied to various kinds of pathological tests. Conventional pathological tests require a lot of work and various kinds of equipment. In order to rapidly perform a test, skilled clinical pathologists are required. However, even if clinical pathologists have required skill, it is difficult to perform various kinds of tests at the same time. However, in a diagnosis of an emergency patient, a rapid test result is very important for timely treatment of the patient. Thus, there is a need to develop an apparatus that can rapidly and accurately and simultaneously perform various pathological tests according to the necessary situations.

SUMMARY OF THE INVENTION

The present invention provides a disc-shaped microfluidic device in which an immunoassay and a biochemical analysis having different processes can be simultaneously conducted and a microfluidic system including the disc-shaped microfluidic device.

The present invention provides a device in which several kinds of test units simultaneously perform desired function when a common process is involved in the function performed by different test units and one test unit does not affect the operations of other test units when a unique process for each test is performed so that different pathological tests can be quickly and accurately conducted within one disc-shaped microfluidic device.

According to an aspect of the present invention, there is provided a microfluidic device for simultaneously conducting two or more assays, the device comprising: a platform which can be rotated; a first assay unit which is disposed at one portion of the platform and detects a first target material from a biological fluid sample, wherein the detecting the target material is carried out using a surface ("capture probe-bound surface") to which a capture probe which selectively binds to the target material is attached; and a second assay unit which is disposed at another portion of the platform and detects a second target material in the biological fluid sample by a reaction using a reagent which reacts with the second target material, wherein the reagent is previously loaded in the second assay unit; wherein each of the first and second units comprises a microfluidic structure which includes a plurality of chambers, a plurality of channels for connecting the plurality of chambers, and a plurality of valves for controlling the flow of a fluid through the channels; and wherein the plurality of valves comprise at least one phase transition valve comprising a valve material in which heat-generating particles are dispersed in a phase transition material that is in a solid state at a room temperature and in a liquefied state at a temperature higher than the melting point of the phase transition material, and the valve material changing into a molten state, when energy is applied to the heat-generating particles, resulting in opening or closing its corresponding channel path.

The first unit may be an immunoassay unit and the second unit may be a biochemical analysis unit. The first target material and the second target material may be the same of different. In embodiments of the present invention, the first target material is different from the second target material, and thus different target materials may be simultaneously assayed in one device.

According to another embodiment, there is provided a disc-shaped microfluidic device for simultaneously conducting immunoassay and biochemistry analysis, the device comprising: a disc-shaped platform which can be rotated; an immunoassay unit which is disposed at one portion of the disc-shaped platform and detects a target material from a sample using surface on which a capture probe selectively combined with the target material is bound; and a biochemistry analysis unit which is disposed at another portion of the disc-shaped platform and detects a target material included in the sample by a biochemical reaction of the sample and a previously-stored reagent, wherein each of the immunoassay unit and the biochemistry analysis unit comprises a microfluidic structure which includes a plurality of chambers, a plurality of channels for connecting the plurality of chambers, and a plurality of valves for controlling the flow of a fluid through the channels, and the plurality of valves comprise at least one phase transition valve comprising a valve material in which heat-generating particles are dispersed in a phase transition material that is in a solid state at room temperatures and in a liquefied state at high temperatures, and the valve material changing into a molten state by energy applied to the heat-generating particles. The heat-generating particles generate heat when an electromagnetic beam is radiated to them from an external energy source, resulting in opening or closing corresponding channel path.

The capture probe-bound-surface is provided by at least one of surfaces of microparticles accommodated in the microfluidic structure, a surface of a microarray chip mounted in the microfluidic structure, and an inner surface of at least one of the plurality of chambers.

The phase transition material may be at least one material selected from the group consisting of wax, gel, and thermoplastic resin. The heat-generating particles may have a diameter of 1 nm to 100 µm. The heat generating particles may comprise a core which absorbs an externally generated electromagnetic beam to change the electromagnetic beam into a heat energy and a shell encompassing the core. The heat generating particles may be at least one selected from the group consisting of polymer beads, quantum dots, Au nanoparticles, Ag nanoparticles, beads with metal composition, carbon particles, and magnetic beads.

The immunoassay unit may comprise: microfluidic particles which are included within the microfluidic structure and provide the capture probe-bound-surface; and a detection probe which is included within the microfluidic structure, is selectively combined with the target material, and includes a material needed for optical signal revelation, wherein the microfluidic structure allows the microparticles, the sample, and the detection probe to react by mixing them and cleans and separates the microparticles in which the reaction is completed. The immunoassay unit may further comprise a reagent which is included in the microfluidic structure, is mixed with the cleaned and separated microparticles and reacts with the optical signal revelation material of the detection probe attached to the target material to generate an optical signal.

The phase transition valve may comprise: an opening valve which is disposed so that a valve plug closes the path at an initial stage, and which, when the valve plug is melted by heat, moves to a drain chamber disposed to be adjacent to an initial position of the valve plug so as to open the path; and a closing valve which includes a valve chamber connected to the path and a valve material inserted in the valve chamber in an initial state, wherein if the valve material is melted and expands by heat, the valve material enters the path, is solidified and closes the path.

The microfluidic structure of the immunoassay unit may comprise: a sample chamber in which a sample is accommodated; a buffer chamber in which a buffer solution is accommodated; a microfluidic chamber in which a microfluidic solution is accommodated; a mixing chamber in which a solution for the detection probe is accommodated, and which is connected to the sample chamber, the buffer chamber, and the microfluidic chamber, respectively, through channels, has an outlet disposed furthest from the center of the disc-shaped platform, and performs reaction of the sample and the microparticles, cleaning and separation of the microparticles using the buffer solution according to control of valves disposed at the respective channels and outlets; a waste chamber which is connected to a portion adjacent to the outlet of the mixing chamber and in which the fluid exhausted from the mixing chamber is accommodated according to control of the valves disposed at the paths; and an optical signal revelation chamber which is connected to the outlets of the mixing chamber through the channels, accommodates the separated microparticles, and provides an optical signal generated by the detection probe.

The mixing chamber may be disposed further from the center of the disc-shaped platform than the sample chamber, the buffer chamber, and the microparticle chamber and is disposed closer to the center of the disc-shaped platform than the waste chamber and the optical signal revelation chamber. A channel for connecting the mixing chamber and the waste chamber may be connected to a position in which a space in which the microparticles are deposited is formed between the connection portion of the mixing chamber and the outlet of the mixing chamber.

The channel for connecting the mixing chamber and the waste chamber may be opened and closed by the valves. The channel for connecting the mixing chamber and the waste chamber may be constituted so that opening and closing operations are repeatedly performed using valves at least twice.

Channels for connecting the buffer chamber and the mixing chamber may be connected to positions corresponding to several levels of the buffer chamber, and valves that operate separately are disposed at each of the channels. The microparticles may be magnetic beads, and the immunoassay unit may be disposed adjacent to the optical signal revelation chamber and include a material used in forming a magnetic field for condensing magnetic beads within the optical signal revelation chamber by a magnetic force.

The immunoassay unit may further comprise a reagent which is accommodated in the optical signal revelation chamber, is mixed with the cleaned and separated microparticles, and reacts the optical signal revelation material of the detection probe attached to target protein to generate an optical signal. The microfluidic structure of the immunoassay unit may further comprise a fixing chamber which is disposed further from the center of the disc-shaped platform than the optical signal revelation chamber and is connected to an outlet of the optical signal revelation chamber, wherein a fixing solution is disposed inside the fixing chamber to stop a reaction of the optical signal revelation material and the reagent.

The microfluidic structure of the immunoassay unit may further comprise a centrifugal separation unit which is connected to the sample chamber and the mixing chamber, centrifugally separates the sample accommodated in the sample chamber, and provides a supernatant of the sample to the mixing chamber.

According to another aspect of the present invention, there is provided a microfluidic device for conducting multiple biological assays simultaneously, the device comprising: a platform which can be rotated; a first assay unit which is disposed at one portion of the platform and detects a first target material from a biological sample using a microarray chip having capture probes arranged on its surface; and a second assay unit which is disposed at another portion of the platform and detects a second target material included in the sample by a reaction of the sample and a previously-loaded reagent which selectively reacts with the second target material, wherein the first assay unit comprises a microfluidic structure which includes a plurality of chambers, a plurality of channels for connecting the plurality of chambers, and a plurality of valves for controlling the flow of a fluid through the channels by rotation of the platform and the valves, and the plurality of valves comprise at least one phase transition valve comprising a valve material in which heat-generating particles are dispersed in a phase transition material, in which that the phase transition material is in a solid state at a room temperature and in a liquefied state at a temperature higher than the melting point of the phase transition material, and the valve material changing into a molten state by heat generated due to energy applied to the heat-generating particles, resulting in opening or closing its corresponding channel path.

In an embodiment, there is provided a disc-shaped microfluidic device for conducting immunoassay and biochemistry analysis simultaneously, the device comprising: a disc-shaped platform which can be rotated; an immunoassay unit which is disposed at one portion of the disc-shaped platform and detects various target proteins from a sample using a microarray chip having capture probes arranged on its surface; and a biochemistry analysis unit which is disposed at another portion of the disc-shaped platform and detects a target material included in the sample by a biochemical reaction of the sample and a previously-stored reagent, wherein the immunoassay unit comprises a microfluidic structure which includes a plurality of chambers, a plurality of channels for connecting the plurality of chambers, and a plurality of valves for controlling the flow of a fluid through the channels and manipulates a fluidic sample by rotation of the disc-shaped platform and the valves, and the plurality of valves comprise at least one phase transition valve comprising a valve material in which heat-generating particles are dispersed in a phase transition material that is in a solid state at room temperature and in a liquefied state at high temperatures, and the valve material moving in a molten state by heat generated due to an electromagnetic beam radiated from an external energy source, in order to open or close its corresponding channel path.

The microarray chip may be mounted on the disc-shaped platform so that capture probes bound on its surface are in contact with the sample inside the microfluidic structure.

The microfluidic structure of the biochemical analysis unit may comprise: a sample chamber in which a sample is accommodated; a reaction chamber which is connected to the sample chamber and in which a reagent for detecting a target material through a biochemical reaction is accommodated; and a detection chamber in which a reaction resultant of the sample and the reagent is accommodated to be optically detected.

The microfluidic structure of the biochemical analysis unit may further comprise a centrifugal separator which is connected to the sample chamber and the reaction chamber, centrifugally separates the sample accommodated in the sample chamber, and provides a supernatant of the sample to the reaction chamber.

According to another aspect of the present invention, there is provided a disc-shaped microfluidic device for conducting immunoassay and biochemistry analysis simultaneously, the device comprising: a disc-shaped platform which can be rotated; a centrifugal separation unit which is disposed close to the center of the disc-shaped platform, centrifugally separates the sample using a centrifugal force generated by rotation of the disc-shaped platform and exhausts a supernatant of the sample; a distribution unit which distributes the supernatant of the sample exhausted from the centrifugal separation unit into a plurality of metering chambers in predetermined amounts; an immunoassay unit which is disposed at one portion of the disc-shaped platform, includes a plurality of chambers, a plurality of channels for connecting the chambers, and a plurality of valves for controlling the flow of a fluid through the channels, immunoassay unit detecting a target material from the sample supplied by the distribution unit using a capture probe-bound-surface; and a biochemistry analysis unit which is disposed at another portion of the disc-shaped platform and detects a target material included in the sample by a biochemical reaction of the sample and a previously-accommodated reagent, wherein the plurality of valves comprise a valve material in which heat-generating particles are dispersed in a phase transition material that is in a solid state at room temperatures and in a liquefied state at high temperatures, and at least one phase transition valve in which the valve material is moved in a molten state by heat generated due to an electromagnetic beam radiated from an external energy source, each phase transition valve opening or closing its corresponding channel path.

The distribution unit may comprise: a distribution channel which is connected to an outlet valve of the centrifugal separation unit, extends along a circumferential direction of the disc-shaped platform, and has a constant fluid resistance over all sections; a plurality of metering chambers which are disposed further from the center of the disc-shaped platform than the distribution channel in a radius direction within the disc-shaped platform; and a plurality of inlet channels which connect the distribution channel to the plurality of metering chambers, wherein the distribution unit distributes the supernatant of the sample exhausted from the centrifugal separation unit to the plurality of metering chambers through the distribution channel using centrifugal force generated by rotation of the disc-shaped platform.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

The above and other features and advantages of the present invention will become more apparent by describing in detail exemplary embodiments thereof with reference to the attached drawings in which.

DETAILED DESCRIPTION OF THE INVENTION

Figure 1:
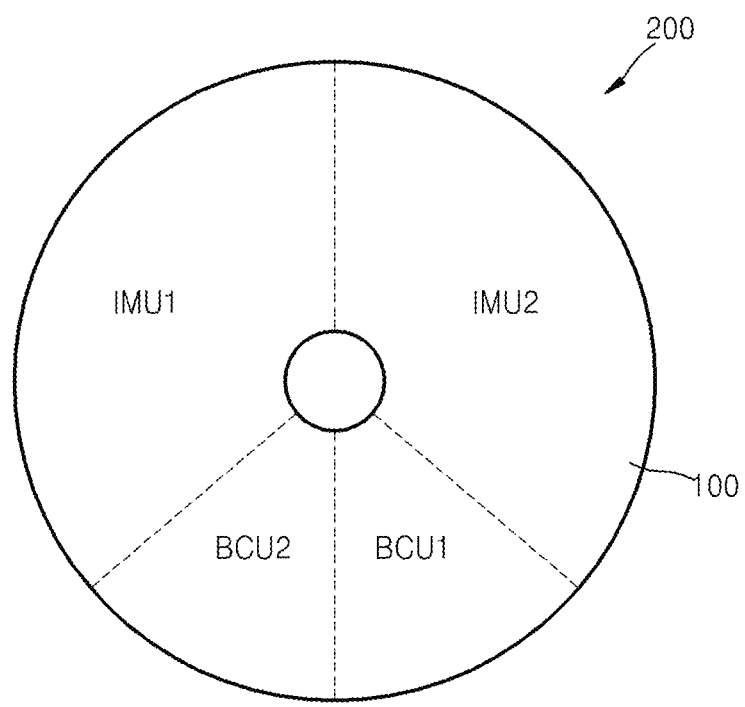
FIG. 1 is a schematic view of a disc-shaped microfluidic device according to an embodiment of the present invention.

The present invention will now be described more fully with reference to the accompanying drawings, in which exemplary embodiments of the invention are shown. Like reference numerals in the drawings denote like elements, and thus their description will not be repeated. The shapes of chambers and channels may be simplified, and the ratio of their sizes may be increased or reduced as compared to reality. In the expressions such as a microarray chip, a microfluidic device, and a micro-particle, 'micro-' is just used having the opposite meaning to 'macro-' and should not be construed as being limiting the sizes of these elements.

The term 'microfluidic structure' employed in the present specification does not indicate a particularly shaped structure but indicates a microstructure comprising a plurality of chambers, channels, and valves, which accommodates a fluid and controls of the flow of the fluid. Thus, the 'microfluidic structure' may constitute units which perform different functions according to the features of arrangement of chambers, channels, and valves and the types of materials accommodated therein.

A 'reagent' in the present specification is used to indicate any kinds of agents, which can be used in the form of a solution and which can produce an optically detectable reactant by a reaction with a sample. In order to classify a reagent used for an immunoassay and a reagent used for a biochemical analysis, the reagent used for (or suitable for) the biochemical analysis is referred to as a 'biochemical reagent' for convenience.

The biological fluid or biological sample fluid which can be tested according to the present invention include, but is not limited to, blood, serum, plasma, urine, sweat, tear fluid, semen, saliva, cerebral spinal fluid, or a purified or modified derivative thereof. The sample may also be obtained from a plant, animal tissue, cellular lysate, cell culture, microbial sample, or soil sample, for example. The sample may be purified or pre-treated if necessary before testing, to remove substances that might otherwise interfere with the testing. Typically, the sample fluid will be an aqueous solution of, for example, polypeptides, polynucleotides, and salts. The solution may include surfactants or detergents to improve solubility of the target substance (or analyte). For non-polar and hydrophobic analytes, organic solvents may be more suitable.

FIG. 1 is a schematic view of a disc-shaped microfluidic device according to an embodiment of the present invention. According to the present embodiment, the disc-shaped microfluidic device 200 comprises at least one immunoassay unit IMU1 and IMU2 and at least one biochemical analysis unit BCU1 and BCU2 in a disc-shaped platform 100 which can be rotated.

Here, the disc-shaped platform 100 is not limited to one having a disc shape but includes one of a fan shape in which the platform 100 is seated on a rotatable frame and can rotate. The disc-shaped platform 100 may be formed of a plastic material of which formation is easy and surface is biologically non-activated, such as polymethylmethacrylate (PMMA), polydimethylsiloxane (PDMS) or polycarbonate (PC). The material of the disc-shaped platform 100 is not limited to them and any material may be used as long as they have chemical and biological stability, optical transparency, and mechanical workability. The disc-shaped platform 100 can be constructed with two or more disc-shaped plates. An engraved structure corresponding to a chamber or a channel is formed on a surface of one plate facing the other plate, and the plates are bonded to provide a space and a path inside the resulting disc-shaped platform 100. The plates of the disc-shaped platform may be bonded using various known methods such as adhesion using an adhesive, a double-sided adhesive tape or ultrasonic wave fusion.

The immunoassay units IMU1 and IMU2 are units which accommodate a biological fluid such as blood or serum separated from blood, manipulate blood or serum within a microfluidic structure (not shown) disposed at a portion of the disc-shaped platform 100 and detect a target material such as an antibody, antigen or protein from biological fluid. Here, each of the immunoassay units IMU1 and IMU2 comprises a microfluidic structure (not shown) comprising a plurality of chambers, a path connecting the chambers and a valve controlling the flow of fluid. The valve may contain at least one phase transition valve, as will be described hereinafter (see FIGS. 9 through 14). The phase transition valve contains a valve material in which heat-generating particles are dispersed into a phase transition material that is in a solid state at room temperatures and in a liquefied state at high temperatures, wherein the valve material is moved in a molten state by heat generated due to an electromagnetic beam radiated from an external energy source in order to open or close the channel path.

The biochemistry analysis units BCU1 and BCU2 are units which accommodate a biological fluid sample such as blood, serum separated from blood, urine or saliva and detect a target material using a biochemical reaction and a reagent. The reagent may be loaded in advance, for example, when the device is fabricated. The reagent chemically reacts with the sample so that the target material can be detected. In the embodiments of the present application described herein, an optical detection is explained. However, one skilled in the art should understand that the signal by reaction of the target material-specific reagents with the biological sample is measured by any suitable detection means, including optical and non-optical methods.

Where the signal is detected optically, detection may be accomplished using any optical detector that is compatible with the spectroscopic properties of the signal. The assay may involve an increase in an optical signal or a decrease. The optical signal may be based on any of a variety of optical principals, including fluorescence, chemiluminescence, light absorbance, circular dichroism, optical rotation, Raman scattering, radioactivity, and light scattering. In an embodiment, the optical signal is based on fluorescence, chemiluminescence, or light absorbance.

In general, the optical signal to be detected will involve absorbance or emission of light having a wavelength between about 180 nm (ultraviolet) and about 50 μm (far infrared). More typically, the wavelength is between about 200 nm (ultraviolet) and about 800 nm (near infrared). A variety of detection apparatus for measuring light having such wavelengths are well known in the art, and include, but not limited to, the use of light filters, photomultipliers, diode-based detectors, and/or charge-coupled detectors (CCD).

Figure 2:
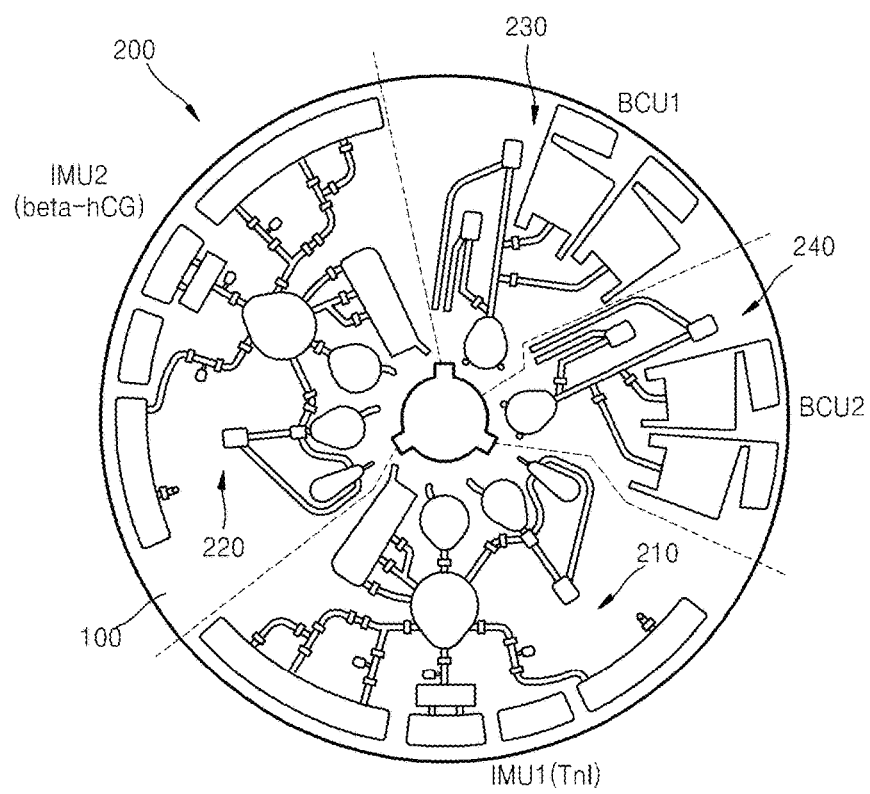
FIG. 2 is a plan view of a disc-shaped microfluidic device having a plurality of immunoassay units and a plurality of biochemical analysis units according to an embodiment of the present invention.

FIG. 2 is a plan view of a disc-shaped microfluidic device having a plurality of immunoassay units and a plurality of biochemistry analysis units according to an embodiment of the present invention. According to the present invention, the disc-shaped microfluidic device 200 comprises a first immunoassay unit (IMU1) 210 for detecting, for example, troponin I (TnI) which is a cardiac marker, a second immunoassay unit (IMU2) 220 for detecting plasma beta-chorionic gonadotropin (beta-hCG) indicating pregnancy, a first biochemistry analysis unit (BCU1) 230 for detecting ALT (Alanine Aminotransferase: GPT) and AST (Aspartate Aminotransferase: GOT) which belong to a liver panel, and a second biochemical analysis unit (BCU2) 240 for detecting amylase and lipase indicating abnormality of a digestive system (in particular, the pancreas).

The above examples are a selected combination of analytes to be quickly tested for the medical treatment of a female emergency patient. However, the present invention is not limited thereto and test items may be added or substituted for other test items if necessary. For example, when a test is conducted on an emergency patient (man), the disc-shaped microfluidic device 200 may comprise an immunoassay unit for detecting plasma B-type natriuretic peptide (BNP) or N-terminal pro-BNP (NT-proBNP) which is a cardiac marker, instead of the immunoassay unit for detecting beta-hCG among the above examples. A doctor may verify regarding a disease in the blood vessel system of a heart through TnI and BNP detection results, verify regarding a liver disease and a liver function through AST and ALT detection results and verify regarding abnormality of the digestive system, in particular, pancreas through amylase and lipase detection results.

In the diagnosis and the medical treatment of a body status of an emergency patient, time required for the above tests is so important in determining the success of the medical treatment. By using the disc-shaped microfluidic device 200 according to the present invention, information on the physical conditions of a patient may be obtained from a small amount of samples within a very short time.

The following Table 1 shows several examples of the combinations of an immunoassay and biochemical analyses which can be conducted simultaneously for a purpose of obtaining information for diagnosing an emergency patient. In addition, various test items may be combined depending on the condition or suspected disease of the patient.

TABLE 1

| Test Fields | Immunoassays | Biochemistry analyses | Remarks |
|---|---|---|---|
| Emergency | Cardiac marker (CK-MB*[1], TnI, myoglobin, pro-BNP), β-hCG | Liver test(ALT, AST), Glucose, Digestive test(amylase, lipase) | Emergency room |

TABLE 1-continued

| Test Fields | Immunoassays | Biochemistry analyses | Remarks |
|---|---|---|---|
| Hepatitis and liver-function examination | HBsAg, Anti-HBs, Anti-HBc, Anti-HCV*[2] | Liver panel(AST, ALT, TB, Albumin, GGT) | General (ALT: chronic hepatitis B patients' regular monitoring items) |
| Blood sugar test | HbA1C | Glucose | General (HbA1C: provision of three-month average blood sugar level) |
| Heart's blood vessel system diseases | Cardiac marker | Liver panel (TC*[3], HDL*[4], LDL*[5], TG*[6]) | Circulatory organ internal medicine |
| Thyroid test | Free T4, TSH*[7] | Glucose | Endocrine internal medicine |

Figure 3:
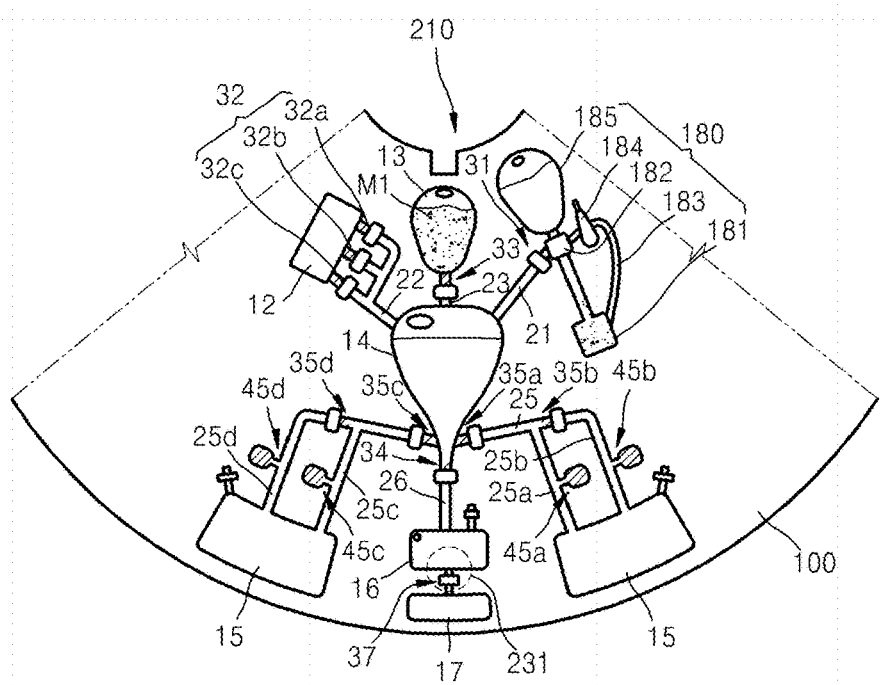
FIG. 3 is a plan view of an immunoassay unit which can be used in the disc-shaped microfluidic device according to an embodiment of the present invention.

*[1]creatine kinase-MB
*[2]Hepatitis C virus
*[3]total cholesterol
*[4]high density lipoprotein
*[5]low density lipoprotein
*[6]triglycerides
*[7]thyroid stimulating hormone FIG. 3 is a plan view of an immunoassay unit which can be used in the disc-shaped microfluidic device according to an embodiment of the present invention. The upper portion of the drawing corresponds to the center of the rotatable disc-shaped platform 100 and the lower portion of the drawing corresponds to the circumference of the disc-shaped platform 100. A microfluidic structure of an immunoassay unit 210 according to the present embodiment comprises a sample chamber 185 in which a fluidic sample is accommodated, a buffer chamber 12 in which a buffer solution is accommodated, and a microfluidic particle chamber 13 in which a microfluidic particle solution containing a large amount of microparticles M1 is accommodated. Each of the sample chamber 185, the buffer chamber 12, and the microfluidic particle chamber 13 is provided with an injection hole or inlet hole, and a user may load the sample, the buffer solution, and the microparticle solution through the injection hole.

A mixing chamber 14 is disposed further from the center of the disc-shaped platform 100 than the three chambers 185, 12, and 13. The mixing chamber 14 is connected to the sample chamber 185, the buffer chamber 12, and the microparticle chamber 13 through channels 21, 22, and 23, respectively, which are fluid flow paths. Valves 31, 32, and 33 for controlling the flow of the fluid are disposed at the channels 21, 22, 23, respectively. The three valves 31, 32, and 33 may be opening valves which are closed at an initial stage and are opened under predetermined conditions. The mixing chamber 14 has an outlet that is disposed furthest from the center of the disc-shaped platform 100, and a valve 34 (hereinafter, referred to as an "outlet valve") is disposed at the outlet of the mixing chamber 14. The cross-sectional width of the mixing chamber 14 may gradually decrease as it is towards radially outward of the disc-shaped platform 100. That is, the cross-sectional width of the mixing chamber 14 that is close to the outlet valve 34 may be smaller. To this end, a portion of an inside of the outlet valve 34 may also be channel-shaped. A previously-loaded detection probe solution (or detection agent solution) is accommodated in the mixing chamber 14, the sample is supplied to the mixing chamber 14 from the sample chamber 185, the microparticle M1 solution is supplied to the mixing chamber 14 from the microparticle chamber 13, and the buffer solution is supplied to the mixing chamber 14 from the buffer chamber 12.

A waste chamber 15 is disposed further from the center of the disc-shaped platform 100 than the mixing chamber 14. The waste chamber 15 may be connected to a portion that is close to the outlet valve 34 of the mixing chamber 14 through a channel 25, i.e., a portion in which the cross-sectional width of the mixing chamber 14 is small, as described above. A space may be formed between the portion of the mixing chamber 14 where the channel 25 is connected to and the outlet valve 34. The space may accommodate microparticles which may be present in the mixing chamber 14 and collected in the space.

The fluid may flow into the waste chamber 15 from the mixing chamber 14 at least twice. First, a sample residue that has reacted with the microparticles M1 flows in the waste chamber 15 and a buffer solution that has rinsed the microparticles M1 flows in the waste chamber 15. Thus, the channel 25 may comprise a valve which repeatedly performs opening and closing operations at least twice. When a one-time valve for performing only an opening or closing operation once is used, the channel 25 may comprise at least two divergence channels 25a and 25b through which the fluid passes toward the waste chamber 15 from the mixing chamber 14 once each. In addition, the two divergence channels 25a and 25b may be closed after communicating with the fluid once each. To this end, the divergence channels 25a and 25b may comprise opening valves 35a and 35b and closing valves 45a and 45b, respectively.

In addition, an optical signal revelation chamber 16 is disposed further from the center of the disc-shaped platform 100 than the outlet of the mixing chamber 14. The optical signal revelation chamber 16 is connected to an outlet valve 34 of the mixing chamber 14 through a channel 26. The optical signal revelation chamber 16 may accommodate a previously-loaded target material-specific reagent so that the reagent can react with an optical signal-producing material of the detection probe. The detection probe is bound to the surface of the microparticles M1. The microparticles M1 are also coupled to a target material. The diction probe-microparticle-target material complex enters the optical signal revelation chamber 16. Upon reaction with the reagent and the optical signal-producing material of the detection probe, an optical signal is generated. A substrate or enzyme that is needed to react with the optical signal revelation material of the detection probe and to generate an optical signal may be included in the reagent.

When the microparticles M1 are magnetic beads, a magnetic material generating a magnetic field, for example, a magnet 231, may be disposed in a portion that is adjacent to the optical signal revelation chamber 16. The magnet 231 may condense the magnetic beads used as the microparticles M1 described above. The magnet 231 may control the position of the magnetic beads by moving to various positions above or below the disc-shaped platform 100. For example, the magnet 231 may play a role for moving the magnet beads that are separated by centrifugal force in the vicinity of the outlet of the mixing chamber 14 to the center of the mixing chamber 14 to be easily dispersed into the solution in the mixing chamber 14.

The buffer chamber 12 may have a large capacity to store a buffer solution in which the microparticles M1 can be rinsed several times (for example, three times), the channel 22 for connecting the buffer chamber 12 and the mixing chamber 14 may diverge into several parts, and the diverged channel parts may be connected to positions corresponding to several levels of the buffer chamber 12. At this time, valves 32a, 32b, and 32c may be provided to the diverged channel parts and may be opening valves that operate separately.

In addition, channels 25c and 25d and valve structures 35c and 35d may be disposed. These channels and valve structures exhaust the fluid to the waste chamber 15 from the mixing chamber 14 depending on the levels of the buffer chamber 12, followed by the closing of the paths. This is because the buffer solution accommodated in the buffer chamber 12 is supplied to the mixing chamber 14 in a predetermined amount so that the microparticles M1 are cleaned and the used buffer separated from the microparticles M1 is exhausted to the waste chamber 15.

The immunoassay units 210 according to the present embodiment may include a centrifugal separation unit 180 including the sample chamber 185. The centrifugal separation unit 180 comprises a supernatant separator 182 that extends from the outlet of the sample chamber 185 toward radially outward of the platform 100 and a particle separator 181 that is connected to the supernatant separator 182 through a channel. One side of the supernatant separator 182 is connected to the mixing chamber 14 through an opening valve 31 and a channel 21. At this time, the particle separator 181 and the supernatant separator 182 may be connected through a bypass channel 183. The bypass channel 183 acts a vent of the particle separator 181. A surplus sample chamber 184 is connected to a portion of the bypass channel 183, and when a surplus amount of sample is loaded into the sample chamber 185, a predetermined amount of a supernatant (e.g., serum) may be supplied to the mixing chamber 14.

Exemplifying the operation of the centrifugal separation unit 180, when whole blood is loaded into the sample chamber 185 and the disc-shaped platform 100 is rotated, heavy blood corpuscles are collected in the particle separator 181 and the supernatant separator 182 is filled with serum. At this time, if the valve 31 of the channel 21 connected to the mixing chamber 14 is opened, serum filled in a portion that is positioned radially inward than the portion of the supernatant separator 182 connected to the channel 21 is conveyed to the mixing chamber 14.

The microfluidic structure of the immunoassay unit 210 according to the present embodiment may further include a fixing member 17 which is connected to the optical signal revelation chamber 16 via a valve 37 disposed therebetween. The fixing chamber 17 may contain a fixing (or quenching) solution for stopping a reaction of a reagent disposed in the optical signal revelation chamber 16 and the optical signal revelation material of the detection probe. By the action of the fixing solution, a reaction for providing an optical signal revelation is stopped and the intensity of the optical signal can be maintained based on a time when the valve 37 is opened and a mixed solution of microparticles including a surface absorption material and the reagent flows. By using this advantage, the proceeding time of the optical signal revelation reaction can be limited. Thus, when the optical signal is detected using an optical detector (not shown), which may be disposed outside the disc-shaped platform 100, an accurate result can be obtained without being affected by its measuring time.

The microparticles M1 have a capture probe which specifically binds to a target material (antigen, antibody or marker protein etc.). The capture probe is coupled to or attached to the surface of the microparticles. The binding between the capture probe and the target material allows to separate the target material from a biological sample. For example, since the capture probe has a specific affinity only to a particular target material, it is useful for detecting a very small amount of the target material included in the sample. The microparticles M1 of which surface is modified with a probe and can be used to separate target materials of interest (e.g., antigen) are commercially available from various sources such as Invitrogen or Qiagen, and examples thereof are DYNABEADS™ Genomic DNA Blood (Invitrogen), NYNABEADS™ anti-*E. coli* O157 (Invitrogen), CELLection™ Biotin Binder Kit (Invitrogen), and MagAttract Virus Min M48 Kit™ (Qiagen). Diphtheria toxin, *Enterococcus faecium, Helicobacter pylori*, HBV, HCV, HIV, Influenza A, Influenza B, Listeria, *Mycoplasma pneumoniae, Pseudomonas* sp., Rubella virus, and Rotavirus may be detected using microparticles to which the particular antibody is attached. A marker protein indicating a heart disease or pregnancy may be detected according to the types of capture probes fixed on the surface of the microparticles, as described above.

The sizes of the microparticles M1 may be 50 nm-1,000 µm. In one embodiment, the microparticles have a size of 1 µm-50 µm. In addition, the microparticles M1 may be formed by mixing microparticles of two or more sizes.

The microparticles M1 may be formed of various materials. In particular, the microparticles M1 may be magnetic beads including at least one of ferromagnetic metals such as Fe, Ni, and Cr and an oxide thereof.

Materials for a detection probe used in a conventional enzyme-linked immunoserological assay (ELISA) process may be used in the protection probe including the optical signal revelation material. For example, when a primary antibody is attached on the surface of the microparticles M1 as a capture probe so as to detect a particular antigen, a secondary antibody to which horseradish peroxidase (HRP) is linked may be used as a detection probe. At this time, a reagent including a substrate and an enzyme of which colors are revealed by a reaction with HRP may be disposed in the optical signal revelation chamber 16.

Figure 4:
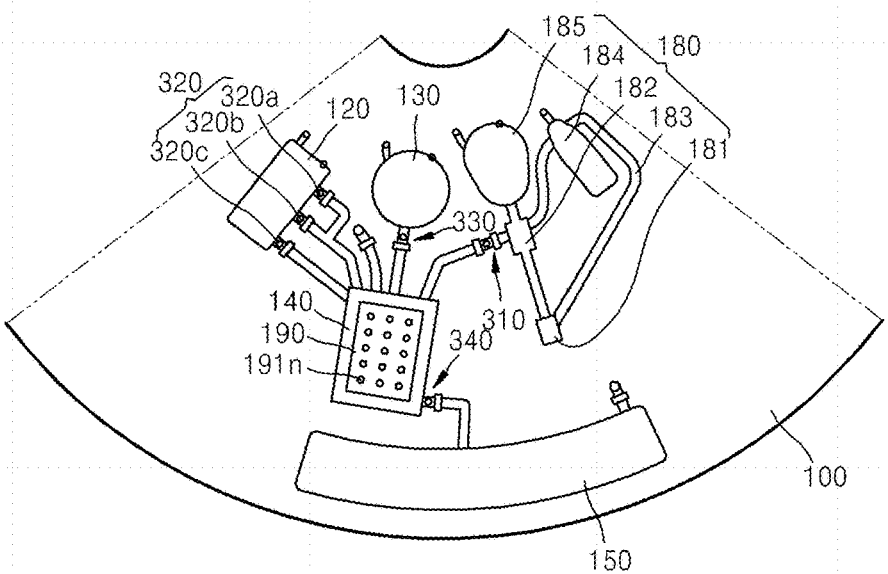
FIG. 4 is a plan view of an immunoassay unit which can be used in the disc-shaped microfluidic device according to another embodiment of the present invention.

FIG. 4 is a plan view of an immunoassay unit which can be used in the disc-shaped microfluidic device according to another embodiment of the present invention. According to the present embodiment, a microfluidic structure including a plurality of chambers 120, 130, 140, and 150, a plurality of paths for connecting the chambers 120, 130, 140, and 150, and a plurality of valves 310, 320, 330, and 340 for controlling the flow of a fluid through each of the paths is disposed within the disc-shaped platform 100. Here, the paths may be channel-shaped.

A microarray chip 190 is mounted on the disc-shaped platform 100 so that a plurality of capture probes 191*n* bound in an array form on the surface of the microarray chip 190 is in contact with a sample (serum) passing a portion of the microfluidic structure.

In the present embodiment, the construction of the microfluidic structure disposed in the disc-shaped platform 100 will now be described. First, the microfluidic structure may include a sample chamber 185 in which a sample such as blood is accommodated, and a centrifugal separation unit 180 which is connected to the sample chamber 185 and separates a supernatant from the sample. In addition, the microfluidic structure may include a reagent chamber 130 for storing a reagent and a buffer solution chamber 120 for storing a buffer solution. The reagent including a material that is selectively bounds to a target material of the sample and provides an optical signal such fluorescence, absorption, and emission may be previously loaded and stored in the reagent chamber 130, and a buffer solution needed to dilute the sample or to clean the surface of the microarray chip 190 contacting the sample may be previously loaded and stored in the buffer solution chamber 120.

The centrifugal separation unit 180, the reagent chamber 130, and the buffer solution chamber 120 are connected to the reaction chamber 140, which is disposed radially outward than the outlets of the centrifugal separation unit 180 and the chambers 120 and 130, via opening valves 310, 320, and 330. The valves 310, 320 and 330 are disposed at the outlet of the unit 180, chamber 120 and chamber 130, respectively. The opening valves 310, 320, and 330 are phase transition valves (see FIGS. 9 and 10) which are disposed so that a valve plug formed of a valve material in which a plurality of heat-generating particles are dispersed in a phase transition material in a solid state at room temperature, closes a flow path at an initial stage, and the valve plug is actively opened by the supply of a driving energy from an external energy source. One wall surface of the reaction chamber 140 may be formed of the microarray chip 190 and the fluidic sample may contact the capture probes 191*n* in front of the microarray chip 190. At this time, the microarray chip 190 may be mounted in various shapes on the disc-shaped platform 100.

A waste chamber 150 is disposed radially outward of the reaction chamber 140. The fluid existing from the reaction chamber 140 is accommodated in the waste chamber 150. An opening valve 340 is disposed at the outlet of the reaction chamber 140 and may confine the fluid within the reaction chamber 140 while a reaction with the sample is performed.

The centrifugal separation unit 180 includes a supernatant separator 182 that extends from the outlet of the sample chamber 185 towards radially outward and a particle separator 181 that is connected to the supernatant separator 182 through a channel. One side of the supernatant separator 182 is connected to the reaction chamber 140 through the opening valve 310 and the channel. At this time, the particle separator 181 and the supernatant separator 182 may be connected around through a bypass channel 183. The bypass channel 183 acts as a vent of the particle separator 181. A surplus sample chamber 184 is connected to a portion of the bypass channel 183, and when a surplus amount of a sample is loaded into the sample chamber 185, a predetermined amount of a supernatant may be supplied to the reaction chamber 140.

A channel for connecting the buffer solution chamber 120 and the reaction chamber 140 is divided into several parts, and the channel parts may be connected to positions corresponding to several levels of the buffer solution chamber 120. At this time, valves 320*a*, 320*b*, and 320*c* may be provided to channel parts and may be opening valves that operate separately. This is because the buffer solution accommodated in the buffer solution chamber 120 is supplied to the reaction chamber 140 by a predetermined amount so that the surface of the microarray chip 190 on which the reaction is completed can be cleaned several times.

Here, the microarray chip 190 may be a microarray chip in which various capture probes 191*n* that capture a target material are bound in an array form on a chip-shaped substrate. For example, the chip-shaped substrate may be formed of glass, silicon or plastics, and the capture probes 191*n* may be protein, cells or other biochemical materials.

An operation of detecting a target material in the immunoassay unit according to the present embodiment will now be described. The following description is directed to an example in which a protein microarray chip is used as the microarray chip 190. The features of the immunoassay unit that can be used in the disc-shaped microfluidic device according to the present invention may be further described. Here, the protein microarray chip is an example of the microarray chip 190 and thus the same reference numeral is used. If whole blood is loaded into the sample chamber 185 and the disc-shaped platform 100 is rotated, heavy blood corpuscles are collected in the particle separator 181 and the supernatant separator 182 is filled with serum. At this time, if the opening valve 310 of the channel connected to the reaction chamber 140 is opened, serum filled in a portion that is closer to the center of rotation (i.e., positioned radially inward) than the portion of the supernatant separator 182 connected to the channel is conveyed to the reaction chamber 140.

The previously-loaded reagent is conveyed to the reaction chamber 140 by opening the opening valve 330 disposed at the outlet of the reagent chamber 130. The reagent may include materials for a detection probe used in a conventional enzyme-linked immunoserological assay (ELISA) process, for example, as an optical signal revelation material. When a primary antibody is bound to the surface of the microarray chip 190 as a capture probe for detecting particular target protein, the reagent may comprise a secondary antibody to which horseradish peroxidase (HRP) as the optical signal revelation material is coupled. At this time, the reagent may include a substrate and an enzyme of which colors are revealed by a reaction with HRP.

A mixed solution of the reagent and serum is in contact with the protein microarray chip 190 in the reaction chamber 140 and is incubated for several minutes to several tens of minutes. As a result, a target protein is captured in the capture probes 191n in which the corresponding target protein exists in the sample, and the secondary antibody (to which the optical signal revelation material is coupled) included in the reagent is attached to the target protein regardless of a temporal order.

After a certain period of time which is sufficient for the completion of the reaction, the opening valve 340 disposed at the outlet of the reaction chamber 140 is opened, and the fluid within the reaction chamber 150 exists into the waste chamber 150 by the action of a centrifugal force. Then, a buffer solution of a predetermined amount is conveyed to the reaction chamber 140 by the action of a centrifugal force whenever the opening valves 320a, 320b, and 320c located to corresponding to several levels of the buffer solution in the buffer solution chamber 120 are sequentially opened, thereby cleaning the surface of the microarray chip 190. The buffer solution which is used to clean the surface of the microarray chip 190 leaves the reaction chamber 140 and enters into the waste chamber 150. The microarray may be fabricated by methods well known in the art.

The microparticles M1 and the microarray chip 190, as discussed above, are explained solely as an example of a medium which carries a capture probe, and the present invention is not limited thereto. Instead of the microparticles M1 and the microarray chip 190, the capture probe may be bound to an inner surface of at least one of the plurality of chambers in the microfluidic structure is used. For example, an inner surface of the mixing chamber 14 in FIG. 3 and an inner surface of the reaction chamber 140 in FIG. 4 can be adopted as the capture probe-bound-surface.

Figure 5:
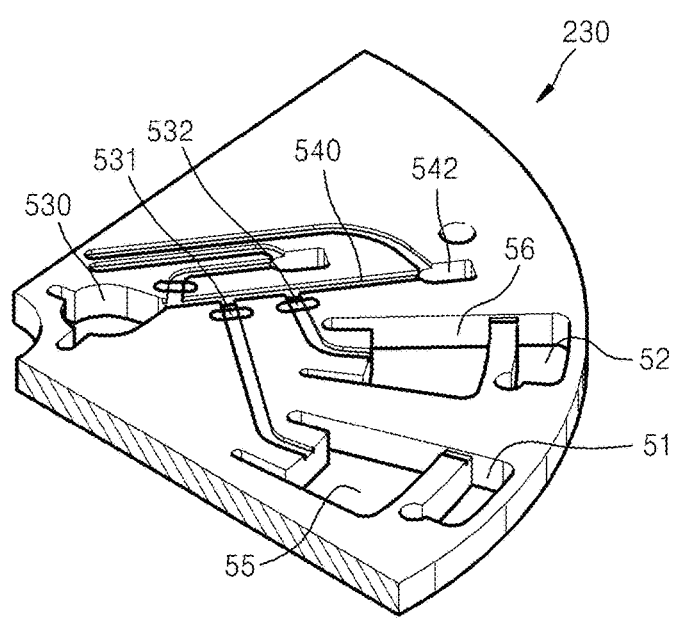
FIG. 5 is a perspective view of a biochemical analysis unit which can be used in the disc-shaped microfluidic device according to another embodiment of the present invention.

FIG. 5 is a perspective view of a biochemical analysis unit which can be used in the disc-shaped microfluidic device according to another embodiment of the present invention. The biochemical analysis unit 230 is constructed in such a way that a biological sample such as serum, urine or salvia reacts with a predetermined biochemical reagent, generating a product of which an optical property such as absorption or fluorescence varies depending on the amount of a target material included in the biological sample. In order to perform an operation of separating serum from blood and the above-described operations, the biochemical analysis unit 230 contains a sample storing portion 530 in which blood is accommodated, a particle separator 542 in which blood corpuscles separated from blood by centrifugal separation are collected, a supernatant separator 540 in which serum separated from blood by centrifugal separation are collected, two outlet valves 531 and 532 which are disposed to distribute a predetermined amount of serum within the supernatant separator 540 into two reaction chambers 55 and 56, respectively, and detection chambers 51 and 52 in which resultant materials generated by a reaction between a previously-loaded biochemical reagent and serum are accommodated respectively. The above-described biochemical analysis unit 230 is just an example of a biochemical analysis unit which can be used in the disc-shaped microfluidic device 200 according an embodiment of the present invention.

Figure 6:
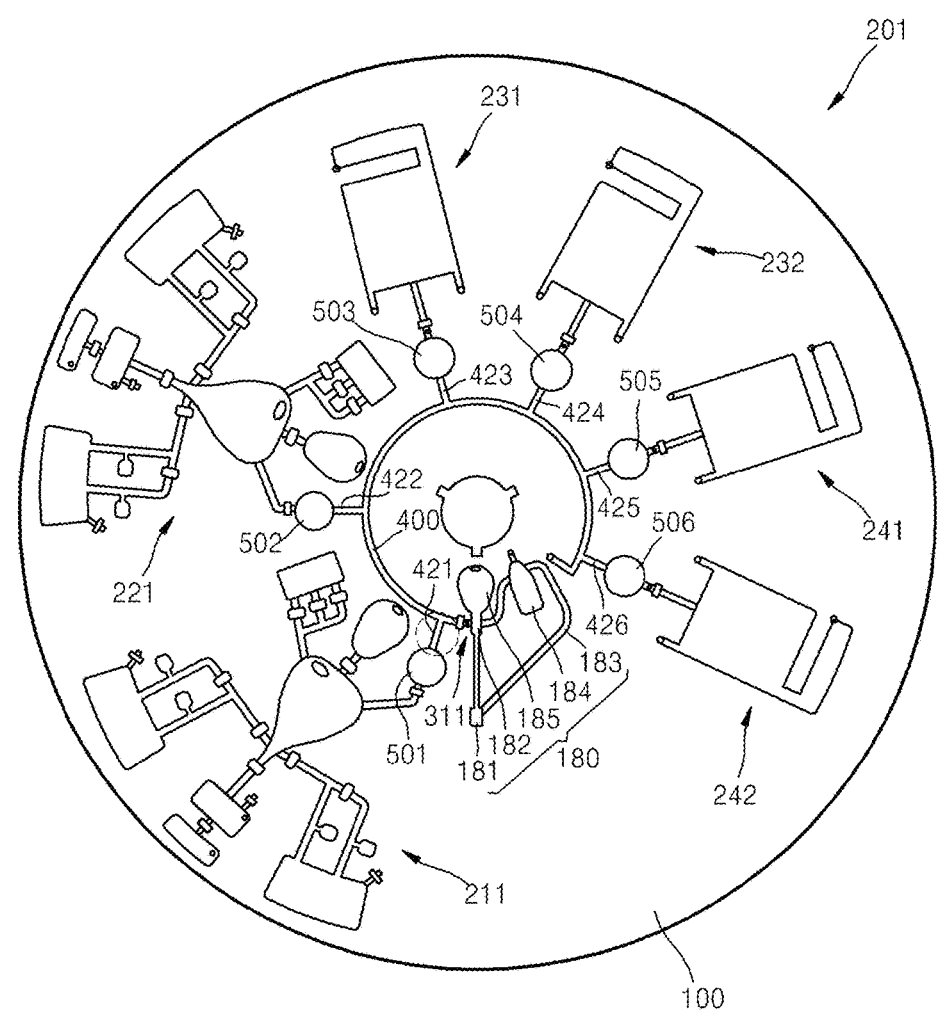
FIG. 6 is a plan view of a disc-shaped microfluidic device including a plurality of immunoassay units and a plurality of biochemical analysis units according to another embodiment of the present invention.

FIG. 6 is a plan view of a disc-shaped microfluidic device including a plurality of immunoassay units and a plurality of biochemical analysis units according to another embodiment of the present invention. The microfluidic device 201 includes a sample chamber 185, a centrifugal separation unit 180 which centrifugally separates a sample accommodated in the sample chamber 185 and exhausts a supernatant of the sample, and a distribution unit which distributes the supernatant of the sample exiting from the centrifugal separation unit 180 into a plurality of metering chambers 501 through 506 by a predetermined amount.

A distribution channel 400 is connected to an outlet valve 311 of the centrifugal separation unit 180. The distribution channel 400 extends from the outlet valve 311 along a circumferential direction of the platform 100. A vent having a vent hole may be connected to the end of the distribution channel 400. The vent hole may be disposed in a position in which the sample does not leak when it is conveyed. The fluid resistance of the distribution channel 400 is constant over all sections from the front end connected to the outlet valve 311 to the rear end connected to the vent. In order to make the fluid resistance constant, the cross-section of the distribution channel 400 may be made constant over all sections. As such, resistance against the movement of a fluid that is subject to be additionally applied when the sample is distributed is minimized so that the sample can be fast and efficiently distributed.

The plurality of sealed metering chambers 501 through to 506 are disposed outside the distribution channel 400 within the platform 100. 'Sealed' means a form in which a vent for exhausting is not disposed in each of the metering chambers 501 through 506. One of the metering chambers 501 through 506 may be disposed in each of the immunoassay units 211 and 221 or the biochemical analysis units 231, 232, 241, and 242. Such a construction enables a biological sample be separated into a supernatant and a precipitate and the supernatant be provided to the plurality of immunoassay units 211 and 221 and the plurality of biochemical analysis units 231, 232, 241, and 242 in a predetermined amount, without manual individual distribution or loading of the sample into each unit in comparison to the embodiments of FIGS. 2 through 5.

The plurality of sealed metering chambers 501 through to 506 are connected to the distribution channel 400 through inlet channels 421 through to 426, respectively. The inlet channels 421 through to 426 and the distribution channel 400 may be connected to one another to be T-shaped, as illustrated in a dotted region of FIG. 6. At this time, the inlet channels 421 through to 426 may be disposed in a radius direction of rotation of the disc-shaped platform 100.

Figure 7:
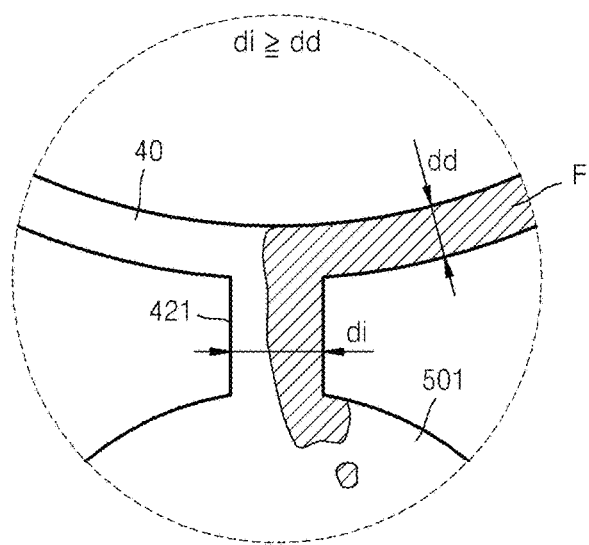
FIG. 7 is an enlarged plan view of the dotted region of FIG. 6 according to one embodiment of the present invention.

FIG. 7 is an enlarged plan view of the dotted region of FIG. 6. An inlet channel 421 having a single channel shape is shown in FIG. 7 as an example of the above-described inlet channels 421 through 426. Most fluid sample supplied to the distribution channel 400 by centrifugal force proceeds toward the metering chamber 501 along the inlet channel 421 in a portion in which the distribution channel 400 and the inlet channel 421 are connected. This is because the direction of the centrifugal force acting on the sample is identical to the direction in which the inlet channel 421 is disposed. The cross-sectional width of the inlet channel 421 may be larger than or the same as the cross-sectional width of the distribution channel 400. This is because, when the fluid sample F supplied through the distribution channel 400 flows into the metering chamber 501, the fluid sample F is not completely filled in the inlet channel 421 but the air in the metering chamber 501 is exhausted through the remaining space. When the depth of the distribution channel 400 and the depth of the inlet channel 421 are the same, the relationship between the width dd of the distribution channel 400 and the width di of the inlet channel 421 may satisfy di≥dd. However, it is not necessary to satisfy this relationship. This is because, even when the inlet channel 421 is clogged by the fluid sample F in the state where a space remains in the metering chamber 501, if the cross-sectional width of the inlet channel 421 is sufficiently large, the centrifugal force acting on the fluid sample F within the inlet channel 421 is larger than the surface tension of the fluid sample F so that the surface of the fluid sample F collapses, the sample is moved into the metering chamber 501 in the form of droplets and the bubbles of a volume corresponding to the droplet-shaped sample are moved to the distribution channel 400.

When one metering chamber 501 is completely filled through the above-described operation, the fluid sample F does not flow in the corresponding metering chamber 501 any more, is further moved along the distribution channel 400 and is filled in the next metering chamber 502. However, even when one metering chamber 501 is not completely filled, part of the fluid sample F may proceed toward the next metering chamber 502.

Figure 8:
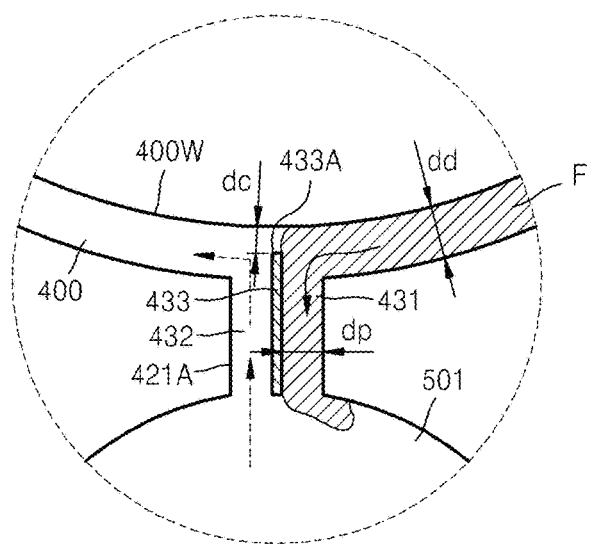
FIG. 8 is an enlarged plan view of the dotted region of FIG. 6 according to another embodiment of the present invention.

FIG. 8 is an enlarged plan view of the dotted region of FIG. 6 according to another embodiment. An inlet channel 421A having a multiple channel shape is shown in FIG. 8 as another example of the above-described inlet channels 421 through to 426. The multiple channel-shaped inlet channel 421A comprises barrier ribs 433 that are disposed in along the lengthwise direction of the middle of the channel. The barrier ribs 433 may be installed so that the flow path in the direction of the distribution channel 400 is intercepted on its inner end 433A. The inlet channel 421A is divided by the barrier ribs 433 into two subchannels 431 and 432. The barrier ribs 433 guide the sample flowing along the distribution channel 400 to first flow to the metering chamber 401 through the subchannel 431 in front of the barrier ribs 433 (based on the flow direction of the fluid sample F). At this time, the air corresponding to the volume of the sample flowing to the metering chamber 501 is exhausted into the distribution channel 400 through the other subchannel 432. When one metering chamber 501 becomes completely filled, the fluid sample F does not flow in the inlet channel 421A but flows along the distribution channel 400 through the inner end 433A of the barrier ribs 433 and inner walls 400W of the distribution channel 400.

The barrier ribs 433 may be installed so that a resistance applied to the fluid sample F when the fluid sample F proceeds toward the subchannel 431 is smaller than or the same as a resistance applied to the fluid sample F when a portion of the distribution channel 400 is clogged by the inner end 433A of the barrier wall and the fluid sample F proceeds along the distribution channel 400. As an example, the cross-sectional width between the inner end 433A of the barrier ribs 433 and the inner walls 400W of the distribution channel 400 may be smaller than or the same as the cross-sectional width of the subchannel 431. In particular, when the depth of the distribution channel 400 and the depth of the inlet channel 421A are the same, the relationship between dc and dp shown in FIG. 6 may satisfy dc≤dp.

Figure 9:
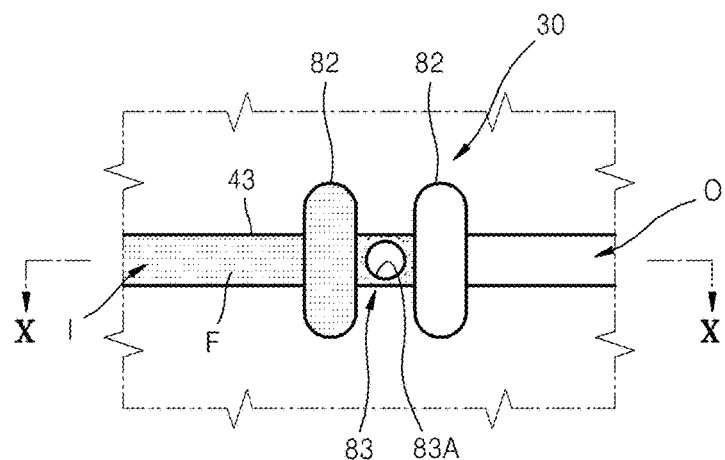
FIG. 9 is a plan view of an opening valve which can be used in the immunoassay unit and the biochemical analysis unit of the disc-shaped microfluidic device according to another embodiment of the present invention.
Figure 10:
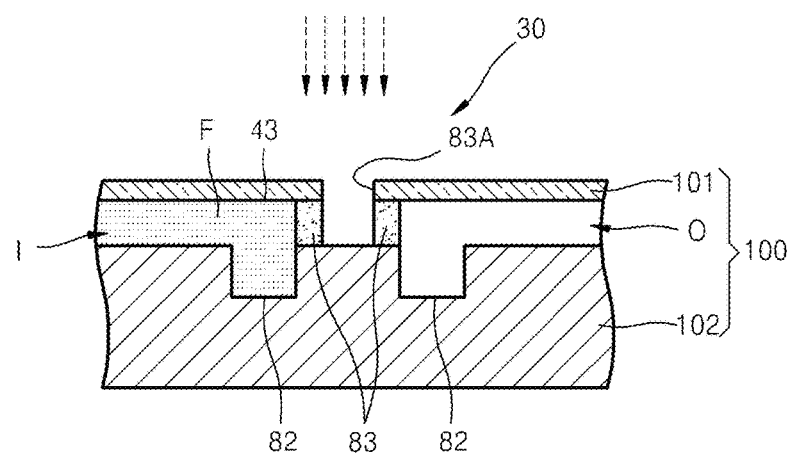
FIG. 10 is a cross-sectional view of the opening valve taken along line X-X' of FIG. 9.

FIG. 9 is a plan view of an opening valve which can be used in the immunoassay unit and the biochemical analysis unit of the disc-shaped microfluidic device according to another embodiment of the present invention, and FIG. 10 is a cross-sectional view of the opening valve taken along line X-X' of FIG. 9. An opening valve 30 comprises a valve plug 83 which is formed of a valve material in a solid state at room temperature. A material in which heat generating particles are dispersed in a phase transition material in a solid state at room temperature can be used as the valve material. A pair of drain chambers 82 having an enlarged width and depth are disposed, to provide space, at the upstream and downstream of a channel 43 adjacent to an initial position in which the solid-state valve plug 83 is disposed.

The valve plug 83 closes a predetermined portion of the channel 43 at room temperature, thereby intercepting the flow of a fluid F that in-flowed from an inlet I. The valve plug 83 is molten at a temperature higher than the melting point of the phase change material contained in the valve, moves to the drain chambers 82 that are respectively adjacent to the upstream and downstream of the channel 43 and is again solidified while opening the flow path of the fluid F. An opening 83A functions as an injection (inlet) hole through which a melted valve material is loaded to form the valve plug 83 when a centrifugal force-based microfluidic device is manufactured.

In order to heat the valve plug 83, an external energy source (not shown) is disposed outside the disc-shaped platform 100, and the external energy source radiates an electromagnetic beam (see dotted arrows of FIG. 10) on the initial position of the valve plug 83, that is, on the opening 83A and a region including the circumference of the valve plug 83. In this case, the external energy source is a laser light source radiating a laser beam, and in this case, the external energy source may include at least one laser diode. The laser light source may radiate a pulse laser having an energy of 1 mJ/pulse or higher, and may radiate a continuous wave laser having an output of 10 mW or higher.

A laser light source, radiating laser light having a wavelength of 808 nm, is used in experiments described with reference to FIGS. 13 through 16. However, the present invention is not limited to the radiation of laser light having the wavelength of 808 nm, and a laser light source radiating laser light having a wavelength of 400-1300 nm can be used as the external energy source of the microfluidic device.

The channel 43 may be provided by cubic patterns that are formed inside the upper plate 101 or the lower plate 102 of the disc-shaped platform 100. The upper plate 101 is formed of an optically transparent material through which an electromagnetic beam radiated by the external energy source is transmitted incident on the valve plug 83, and thus, the flow of the fluid F can be observed from the outside due to the transparency. As an example thereof, glass or transparent plastic materials may be advantageous in view of excellent optical transparency and low manufacturing cost.

The heat generating particles dispersed in the valve plug 83 have a diameter of 1 nm to 100 μm so as to freely flow within the channel 43 having a width of about several thousands of micrometers (μm). The heat generating particles have the characteristic by which, when a laser is radiated on the particles, the temperature of the heat generating particles rapidly rises due to the radiation energy of the laser, and the heat generating particles dissipate heat and are uniformly dispersed in a wax. Also, the heat generating particles may have a structure comprising a core including a metal component and a shell that has a hydrophobic property so as to have the above-described characteristic. For example, the heat generating particles may have a structure comprising a core formed of a ferromagnetic material, such as Fe, and a shell including a plurality of surfactants that are combined with Fe and which encompass Fe. Such a material is usually called a magnetic fluid. Generally, the heat generating particles are kept in a state where the heat generating particles are dispersed in a carrier oil that may also have a hydrophobic property so that the heat generating particles that have a hydrophobic surface structure can be uniformly dispersed. The carrier oil in which the heat generating particles are dispersed is mixed with the wax so that the material of the valve plug 83 can be manufactured. The shape of the heat generating particles is not limited to the shape of as describe above and the heat generating particles can also be polymer beads, quantum dots, Au nanoparticles, Ag nanoparticles, beads with metal composition, carbon particles or magnetic beads. The carbon particles include graphite particles.

A phase transition material used in forming the valve plug 83 may be a wax.

When the energy of the electromagnetic beam is transmitted to the platform, for example to the circumference area, in the form of a heat energy, the wax is melted due to the heat generating particles which absorb the heat energy and has fluidity and as such, the valve plug 83 collapses and the flow path of the fluid F is opened. The wax of the valve plug 83 may have a melting point which is chosen or adjusted to be not too high or not too low. This is because, if the melting point is too high, the wax requires a large amount of time to be melted and it is difficult to precisely control an opening time of the flow path of the fluid F and if the melting point is too low, the wax may partially melt even in the absence of the application of external energy and the fluid F may leak. Also, the wax can be paraffin wax, microcrystalline wax, synthetic wax, natural wax, etc. The phase transition material can also be gel or thermoplastic resin. The gel can be polyacrylamide, polyacrylates, polymethacrylates or polyvinylamides etc. In addition, the thermoplastic resin can be cyclic olefin copolymer (COC), poly(methyl methacrylate) (PMMA), polycarbonate (PC), polystyrene (PS), polyoxymethylene (POM), perfluoroalkoxy (PFA), polyvinylchloride (PVC), polypropylene (PP), polyethylene terephthalate (PET), polyetheretherketone (PEEK), polyacrylate (PA), polysulfone (PSU) or polyvinyldiene fluoride (PVDF).

Figure 11:
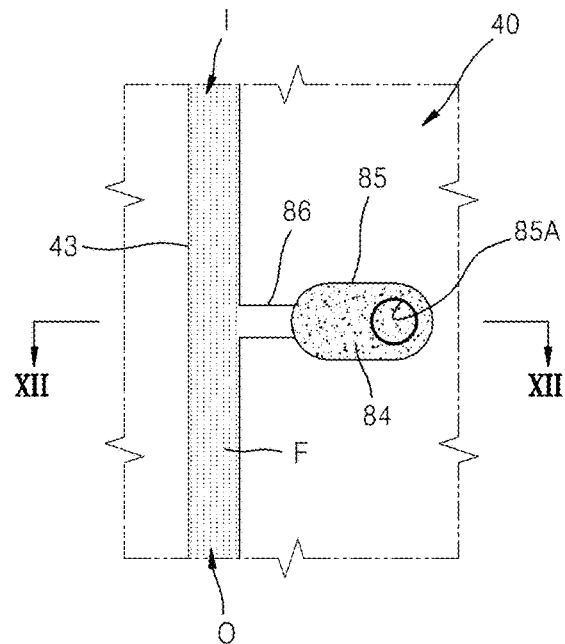
FIG. 11 is a plan view of a closing valve which can be used in the immunoassay unit and the biochemical analysis unit of the microfluidic device according to an embodiment of the present invention.
Figure 12:
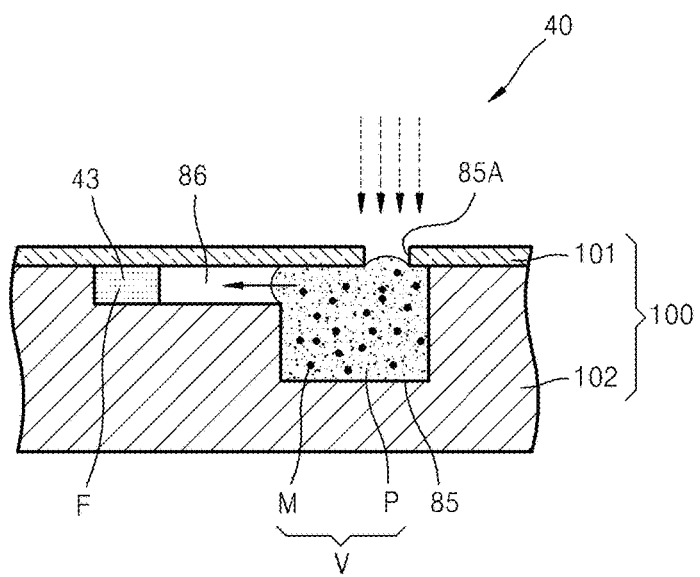
FIG. 12 is a cross-sectional view of the closing valve taken along line XII-XII' of FIG. 11.

FIG. 11 is a plan view of a closing valve which can be used in the immunoassay unit and the biochemical analysis unit of the microfluidic device according to an embodiment of the present invention, and FIG. 12 is a cross-sectional view of the closing valve taken along line XII-XII' of FIG. 11. A closing valve 40 includes a channel 43 having an inlet I and an outlet O, a valve material container 85 connected to the middle of the channel 43, and a valve material V which is inserted in the valve material container 85 in a solid state at room temperature at an initial stage. If the valve material V is heated, the valve material V is melted and expands, enters the channel 43, solidifies again and intercepts the channel 43 through a valve connection path 86.

Like the above-described opening valve 30 of FIG. 9, the closing valve 40 of the present embodiment may also be provided with cubic patterns that are formed inside the upper plate 101 or the lower plate 102 of the disc-shaped platform 100 of the microfluidic device. The upper plate 101 may be formed of an optically transparent material in which an electromagnetic beam radiated by an external energy source (not shown) is transmitted, and thus, a fluid sample F can be observed from the outside due to the transparency. Furthermore, the upper plate 101 may have an opening 85A corresponding to the valve material container 85 so as to function as an injection hole through which the valve material V that melted when the microfluidic device is manufactured is loaded.

The phase transition material P and the heat generating particles M of the valve material V may be the same to those described above with respect to the phase transition opening valve. In addition, the external energy source which provides an electromagnetic beam to the valve material V, may also be the same to those described previously with respect to the phase transition opening valve.

If laser beams are radiated on the valve material V including the phase transition material P and the heat generating particles M, the heat generating particles M absorb energy to heat the phase transition material P. As such, the valve material V is melted, expands, and enters the channel 43 through the valve connection path 86. The valve material V that is solidified again while contacting the fluid F within the fluid collecting channel 150 to form a valve plug so that the flow of the fluid sample F through the channel 43 is controlled.

The result of an experiment in which a reaction time of the above-described valve unit is measured is as follows. The pressure of a working fluid in a test chip for the experiment was kept at 46 kPa. A syringe pump (Havard PHD2000, USA) and a pressure sensor (MPX 5500DP™, Freescale semiconductor Inc., Ariz., USA) were used to keep the pressure constant at 46 kPa. A laser light source having an emission wavelength of 808 nm and an output of 1.5 W is used as an external energy source for radiating an electromagnetic beam to the valve unit. Data on the reaction time of the valve unit was obtained through a result analysis of a high-speed photographing device (Fastcam-1024, Photron, Calif., USA). As a wax, a ferrofluid which is a mixture of a dispersion of magnetic beads of an average diameter of 10 nm as heat generating particles, dispersed in a carrier oil, and a paraffin wax at the ratio of 1:1 is used. That is, a so-called ferrowax that has a volume fraction of a ferrofluid of 50%, was used as the valve material.

Figure 13:
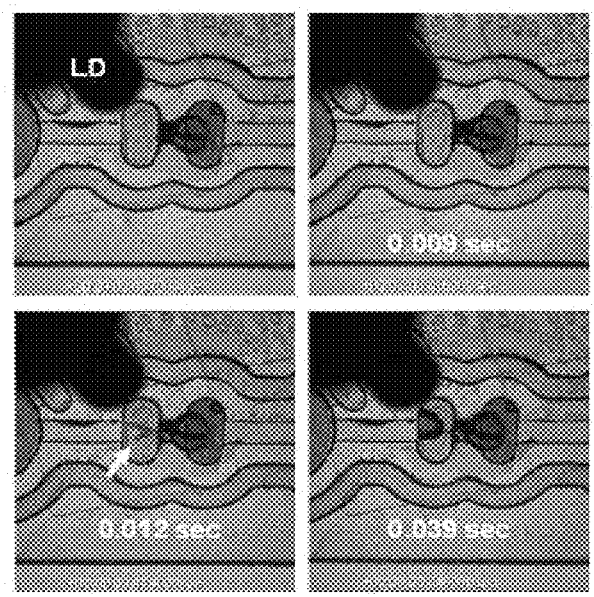
FIG. 13 is a series of high-speed photographs showing the operation of the opening valve of FIG. 9.

FIG. 13 is a series of high-speed photographs showing the operation of the opening valve of FIG. 9. A reaction time, which is the time from when a laser beam starts to be radiated on the valve plug 83 of the opening valve until when the valve plug 83 is melted and the channel 43 is opened, was 0.012 seconds.

Figure 14:
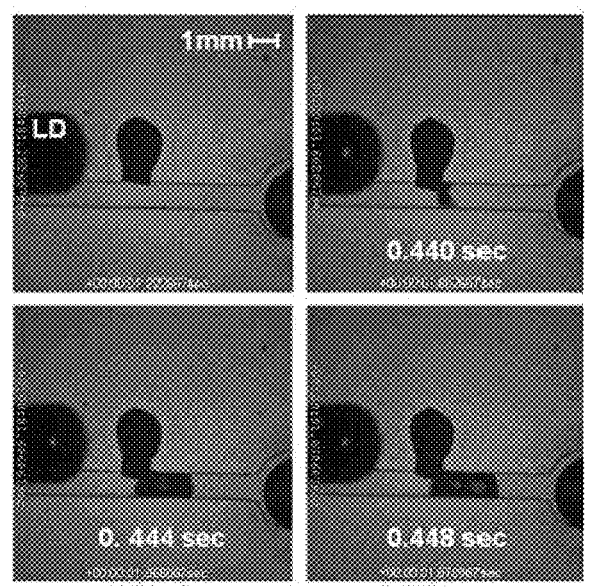
FIG. 14 is a series of high-speed photographs showing the operation of the closing valve of FIG. 11.

FIG. 14 is a series of high-speed photographs showing the operation of the closing valve of FIG. 11. A reaction time, which is the time from when a laser beam starts to be radiated on the valve material of the closing valve until when the valve material is melted and expands and the channel 43 is closed, was 0.444 seconds. Compared to the reaction time of a conventional wax valve of 2-10 seconds, one of ordinary skill in the art can understand that the reaction time is significantly shortened.

Figure 15:
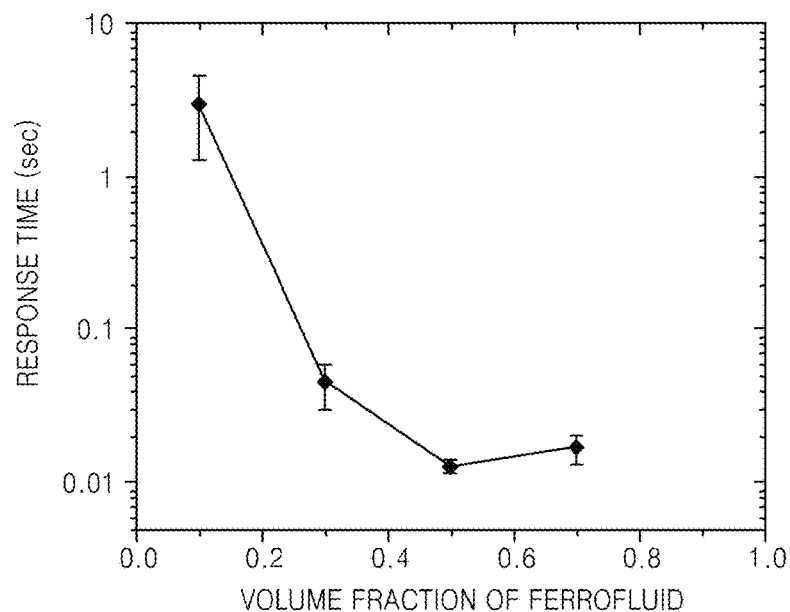
FIG. 15 is a graph showing the volume fraction of a ferrofluid according to a valve reaction time in a valve material used in the open valve of FIG. 9.

FIG. 15 is a graph showing the volume fraction of a ferrofluid according to a valve reaction time in the valve material used in the open valve of FIG. 9. When the volume fraction of the ferrofluid increases, a reaction time is reduced. However, regardless of this, when the volume fraction of the ferrofluid increases to 70% or higher, the maximum hold-up pressure of the valve plug tends to be reduced. Thus, the volume fraction of the ferrofluid that is to be included in the valve plug in the valve unit is determined by compromising a demand for a reaction time and a demand for maximum hold-up pressure.

Figure 16:
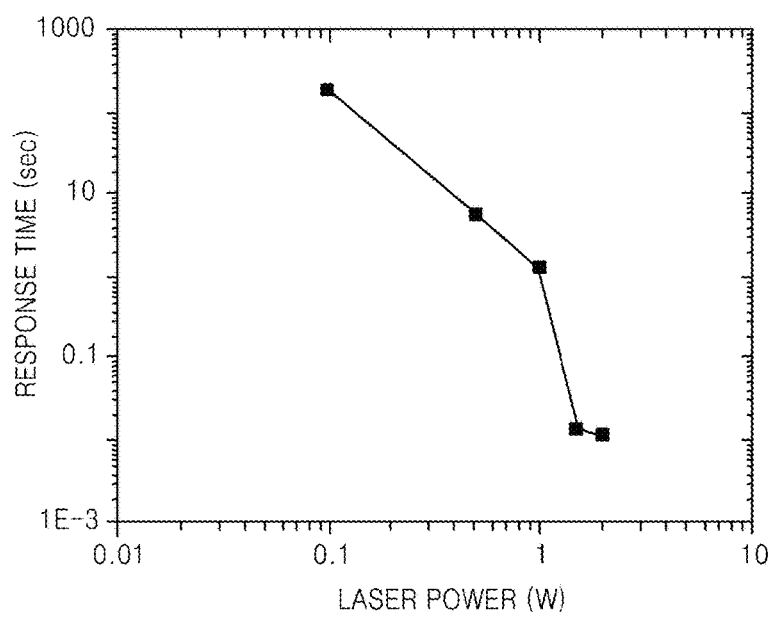
FIG. 16 is a graph showing power of a laser light source that is used as an external energy source when the opening valve of FIG. 9 is driven, and a valve reaction time, according to an embodiment of the present invention.

FIG. 16 is a graph showing power of a laser light source that is used as an external energy source when the opening valve of FIG. 9 is driven, and a valve reaction time, according to an embodiment of the present invention. As an output of the laser light source increases, a reaction time tends to be reduced. However, if the output of the laser light source is close to 1.5 W, a change in reaction time is subtle, and (although not shown in the graph), if the output of the laser light source exceeds 1.5 W, the reaction time quickly converges towards a predetermined minimum reaction time because thermal conductivity is limited by paraffin wax. In the experiment, for this reason, a laser light source having an output of 1.5 W was used. However, the external energy source of the present invention is not limited to this.

Figure 17:
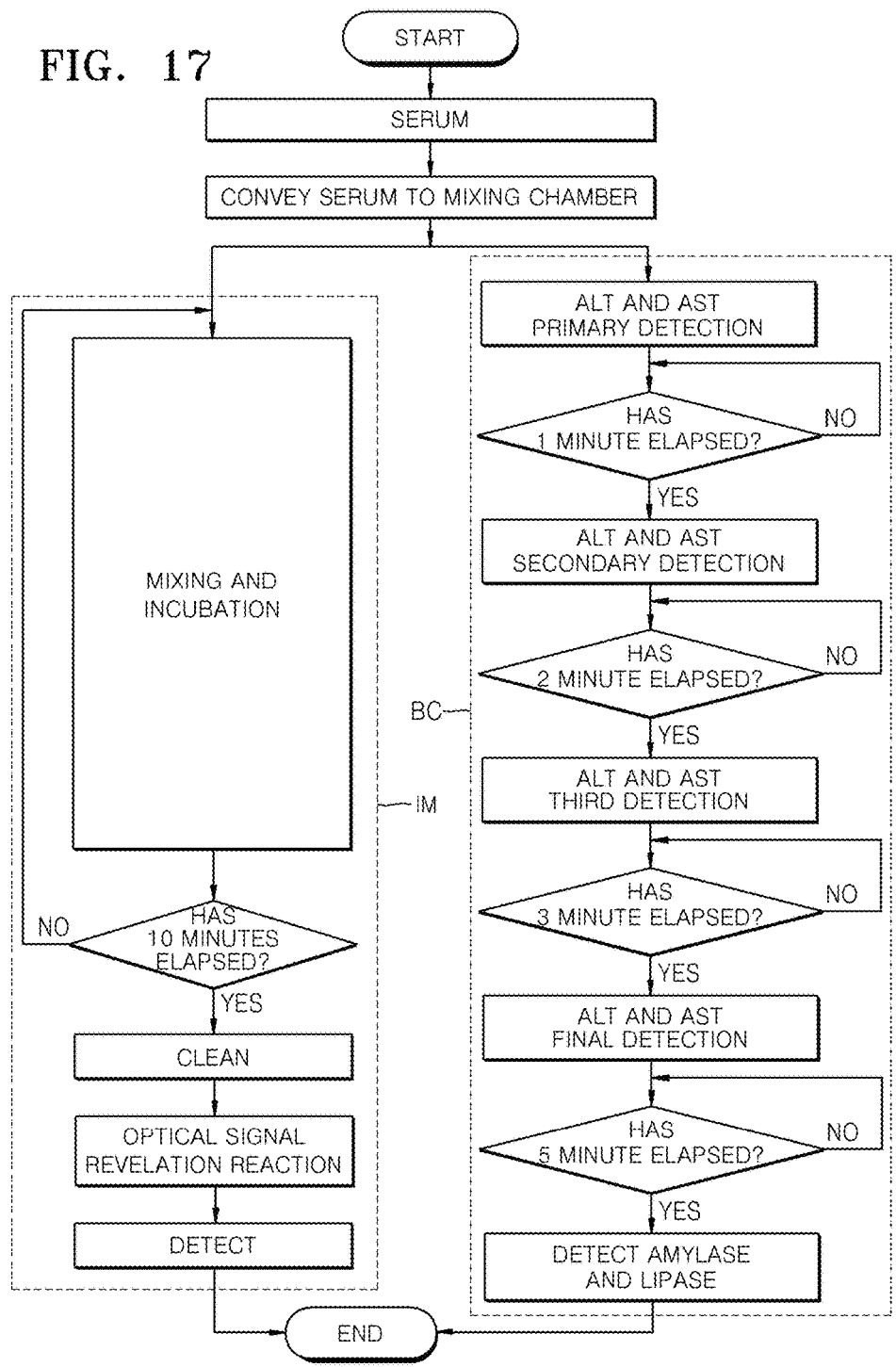
FIG. 17 is a flowchart illustrating a method of conducting an immunoassay and a biochemical analysis using the disc-shaped microfluidic device according to the present invention.

FIG. 17 is a flowchart illustrating a method of conducting an immunoassay and a biochemical analysis using the disc-shaped microfluidic device according to the present invention. The features of the present invention will become more apparent by describing an example of a method of simultaneously driving an immunoassay (IM) unit and a biochemical analysis (BC) unit disposed on one disc-shaped platform.

First, serum is separated from the loaded blood. This operation is common in the IM unit and BC unit and thus may be performed simultaneously in the two units so as to reduce the overall test time. Like in the microfluidic device of FIG. 2, when a centrifugal separation unit is disposed in each test unit, an operation of manual loading of a blood sample into the sample chamber of each unit and of simultaneously separating serum from the blood sample may be performed. In addition, like in the microfluidic device of FIG. 6, when there is a common centrifugal separation unit for supplying separated serum to a plurality of test units, a blood sample may be manually loaded only into the common centrifugal separation unit and a serum separation operation may be performed.

Next, separated serum is conveyed to a mixing chamber of each unit. In the microfluidic device of FIG. 2, a plurality of opening valves disposed in a channel connected to the mixing chamber from each centrifugal separation unit are respectively opened, and in the microfluidic device of FIG. 6, serum is distributed into a plurality of metering chambers from the common centrifugal separation unit and then, opening valves disposed at the outlet of each metering chamber are respectively opened. Conveying of serum is performed by a centrifugal force generated by rotation of a disc-shaped platform after a corresponding valve is opened.

Incubation is performed in the mixing chamber of the IM unit. Although there will be differences depending on the materials to be detected or types of detection probes, it may generally take about 10 minutes to perform the incubation of a particular combination of the material to be detected, a capture probe, and a detection probe. While incubation is performed, a valve disposed at the outlet of the mixing chamber of the IM unit is maintained in a closed state.

While incubation is performed in the IM unit, a biochemical analysis may be conducted by the BC unit. The numbers and interval of detecting signals generated in the BC unit is generally determined depending on the biochemical reaction of the target material to be determined. Thus, in case of ALT and AST tests, the detection data is obtained several times at predetermined time intervals (e.g. 1 min.). On the other hand, in the case of amylase and lipase tests, obtaining of detection data once after a predetermined period of time has elapsed is sufficient. All of the operations may be performed while the incubation step is performed in the IM unit.

When the incubation is finished in the IM unit, microparticles or a microarray chip having a capture probe may be cleaned and a target material (to which the detection probe is attached) attached to the surface of the capture probe may be optically detected. A specific cleaning procedure has been previously introduced in the description of embodiments of an immunoassay unit.

It should be noted that even though various embodiments of the present invention have been described with respect to the detection and assay of different target materials in the respective assay units, the present invention encompasses embodiments where the same target material may be simultaneously detected and/or analyzed in different assay units using different reagents.

According to an embodiment of the present invention, a rotatable microfluidic device in which an immunoassay and a biochemical analysis for various processes can be simultaneously conducted and a microfluidic system including the disc-shaped microfluidic device are provided so that time and effort for performing of pathological tests can be remarkably reduced.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:
1. A microfluidic device for conducting two or more assays, the device comprising:
   a sample chamber which is disposed at the device, and is used for initially loading a sample;
   a first assay structure which is disposed at one location of the device and includes a region in which a capture probe is arranged, the capture probe configured to detect a first target material in a sample via a protein reaction;
   a second assay structure which is disposed at another location of the device and includes a region in which a biochemical reagent is arranged, the biochemical reagent configured to detect a second target material in the sample via a biochemical reaction,
   a distribution channel which extends along a circumferential direction of the device, and has a constant fluid resistance over all sections; and
   a centrifugal separation unit which is disposed radially inward of the distribution channel and disposed between the sample chamber and the distribution channel,
   wherein the centrifugal separation unit is configured to centrifugally separate the sample using a centrifugal force generated by rotation of the device to give a supernatant and a precipitate, wherein the device has a rotational center and the sample is supplied from the sample chamber to the first assay structure and the second assay structure using the centrifugal force due to rotation of the device around the rotational center, and wherein the supernatant of the sample existing from the centrifugal separation unit is distributed to the first assay structure and the second assay structure through the distribution channel using the centrifugal force generated by rotation of the device.

2. The device of claim 1, wherein the first assay structure comprises a microarray chip and the region is a surface of the microarray chip.

3. The device of claim 1, wherein the first assay structure is an immunoassay unit which detects the first target material from the sample and includes a plurality of chambers, a plurality of channels for connecting the plurality of chambers, and a plurality of valves for controlling the flow of a fluid through the channels, wherein at least one of the plurality of the chambers includes microparticles having the capture probe which selectively binds to the first target material is attached.

4. The device of claim 3, wherein the first assay structure comprises a detection probe selectively binds to the first target material, and includes an optical signal revelation material, wherein the first assay structure allows the microparticles, the sample, and the detection probe to react upon mixing.

5. The device of claim 4, wherein the first assay structure comprises a reagent which is mixed with the microparticles and reacts with the optical signal revelation material of the detection probe, said detection probe being attached to the first target material, to generate an optical signal.

6. The device of claim 5, wherein the first assay unit comprises:
   a buffer chamber in which a buffer solution is accommodated;
   a microparticle chamber in which microparticles are accommodated
   a mixing chamber in which a solution for the detection probe is accommodated, and which is connected to a first metering chamber, the buffer chamber, and the microparticle chamber, respectively, through channels, has an outlet disposed radially outward of an inlet of the microfluidic chamber, and performs a reaction of the sample and the microparticles, and a separation of the microparticles using the buffer solution according to operations of valves disposed at the respective channels and outlets, to provide separated microparticles;
   a waste chamber which is connected to a portion adjacent to the outlet of the mixing chamber and in which a fluid existing from the mixing chamber is accommodated according to control of the valves disposed at the paths; and
   an optical signal revelation chamber which is connected to the outlets of the mixing chamber through the channels, accommodates the separated microparticles, and provides the optical signal generated by the detection probe.

7. The device of claim 6, wherein the mixing chamber is disposed radially outward of the sample chamber, the buffer chamber, and the microparticle chamber, and is disposed radially inward of the waste chamber and the optical signal revelation chamber.

8. The device of claim 6, wherein a channel for connecting the mixing chamber and the waste chamber is connected to a connection portion of the mixing chamber, and a space to receive the microparticles from the mixing chamber is formed between the connection portion of the mixing chamber and the outlet of the mixing chamber.

9. The device of claim 6, wherein the first metering chamber provides the supernatant of the sample to the mixing chamber.

10. The device of claim 6, wherein the reagent is accommodated in the optical signal revelation chamber.

11. The device of claim 10, wherein the first assay structure comprises a fixing chamber which is disposed further from the center of the device than the optical signal revelation chamber and is connected to an outlet of the optical signal revelation chamber, wherein a fixing solution is disposed inside the fixing chamber to stop a reaction of the optical signal revelation material and the reagent.

12. The device of claim 1, wherein the second assay structure is a biochemical analysis unit which comprises:
   a reaction chamber which is connected to the second metering chamber and in which the biochemical reagent for detecting the second target material via the biochemical reaction is accommodated; and
   a detection chamber in which a reaction resultant of the sample and the biochemical reagent is accommodated to be optically detected.

13. A disc-shaped microfluidic device for conducting immunoassay and biochemistry analysis simultaneously, the device comprising:
   an immunoassay unit which is disposed at one portion of the device, and comprises a plurality of chambers, a plurality of channels for connecting the chambers, a plurality of valves for controlling the flow of a fluid through the channels, and a microarray chip, the microarray chip comprising a capture probe configured to detect a target protein from a sample; and
   a biochemistry analysis unit which is disposed at another portion of the device and comprises a previously-loaded reagent configured to detects a target material included in the sample, by a biochemical reaction of the sample and the previously-loaded reagent; and
   a sample chamber configured to supply the sample to the immunoassay unit and the biochemistry analysis unit using a centrifugal force generated by rotation of the device.

14. The device of claim 13, wherein the immunoassay unit comprises:
   a buffer chamber comprising a buffer solution;
   wherein the buffer solution is configured to clean microparticles a plurality of times.

15. The device of claim 14, further comprises:
   a centrifugal separation unit configured to centrifugally separate the sample using the centrifugal force generated by rotation of the device to give a supernatant and a precipitate;
   wherein the separated sample is contacted to the microarray chip.

16. The device of claim 15, further comprises:
   a reagent chamber configured to store a reagent that selectively bounds to the target protein and provides an optical signal,
   wherein the centrifugal separation unit, the reagent chamber and the buffer chamber are respectively connected to a reaction chamber having the microarray chip.

17. A disc-shaped microfluidic device for conducting immunoassay and biochemistry analysis simultaneously, the device comprising:

a centrifugal separation unit which is disposed radially inward of all other units provided in the device and centrifugally separates a sample using a centrifugal force generated by rotation of the disc-shaped device to give a supernatant and a precipitate;

a distribution unit which distributes the supernatant of the sample from the centrifugal separation unit into a plurality of metering chambers in a predetermined amount;

an immunoassay unit which is disposed at one portion of the disc-shaped device, includes a plurality of chambers, a plurality of channels for connecting the chambers, and a plurality of valves for controlling the flow of a fluid through the channels, the immunoassay unit detecting a first target material from the sample supplied by the distribution unit using a microparticle having capture probe; and a biochemistry analysis unit which is disposed at another portion of the disc-shaped device and detects a second target material included in the sample, supplied by the distribution unit, by a biochemical reaction of the sample and a previously-loaded reagent;

a sample chamber which is connected to the immunoassay unit and the biochemistry analysis unit through the a centrifugal separation unit and the distribution unit, wherein the device has a rotational center and the sample is supplied from the sample chamber to the immunoassay unit and the biochemistry analysis unit using the centrifugal force due to rotation of the device around the rotational center.

18. A method of conducting an immunoassay and a biochemical analysis simultaneously using a disc-shaped microfluidic device having a sample chamber, an immunoassay unit for conducting the immunoassay and a biochemical analysis unit for conducting the biochemical analysis, the method comprising:

supplying the sample from the sample chamber to a centrifugal separation unit;

separating the sample using a centrifugal force generated by rotation of the device to give a supernatant and a precipitate in the centrifugal separation unit;

distributing the supernatant to the immunoassay unit via a first metering chamber disposed between the immunoassay unit and the centrifugal separation unit and to the biochemistry analysis unit via a second metering chamber disposed between the biochemistry analysis unit and the centrifugal separation unit; and detecting a first target material using a capture probe which is arranged in the immunoassay unit and a second target material using a biochemical reagent which is accommodated in the biochemistry analysis unit, wherein the device has a rotational center and the distributing the supernatant comprises distributing the supernatant to the immunoassay unit and the biochemistry analysis unit using the centrifugal force due to rotation of the device around the rotational center.

19. The method of the claim 18, wherein the detecting comprises:

mixing the supernatant, the capture probe and a detection probe including an optical signal revelation.

20. The method of the claim 18, wherein the detecting comprises:

mixing the supernatant and a biochemical reagent.

* * * * *